United States Patent
Mendyk

(10) Patent No.: US 11,690,784 B2
(45) Date of Patent: Jul. 4, 2023

(54) BIOPHARMACEUTICAL CONTAINER, BIOPHARMACEUTICAL CONTAINER BAG, AND METHOD FOR THE PRODUCTION AND USE OF SAID BIOPHARMACEUTICAL CONTAINER

(71) Applicant: SARTORIUS STEDIM FMT SAS, Aubagne (FR)

(72) Inventor: Nicolas Mendyk, Peypin (FR)

(73) Assignee: SARTORIUS STEDIM FMT SAS, Aubagne (FR)

( * ) Notice: Subject to any disclaimer, the term of this patent is extended or adjusted under 35 U.S.C. 154(b) by 938 days.

(21) Appl. No.: 16/319,388

(22) PCT Filed: Jul. 12, 2017

(86) PCT No.: PCT/FR2017/000141
§ 371 (c)(1),
(2) Date: Jan. 21, 2019

(87) PCT Pub. No.: WO2018/015618
PCT Pub. Date: Jan. 25, 2018

(65) Prior Publication Data
US 2019/0274922 A1    Sep. 12, 2019

(30) Foreign Application Priority Data
Jul. 22, 2016   (FR) ..................... 1670399

(51) Int. Cl.
*A61J 1/10*    (2006.01)
*B29L 31/00*   (2006.01)
(Continued)

(52) U.S. Cl.
CPC ............... *A61J 1/10* (2013.01); *A61J 1/1443* (2013.01); *A61J 1/1475* (2013.01); *A61M 39/10* (2013.01); *B29L 2031/7148* (2013.01)

(58) Field of Classification Search
CPC .......... A61J 1/10; A61J 1/1443; A61J 1/1475; B29L 2031/7148
See application file for complete search history.

(56) References Cited

U.S. PATENT DOCUMENTS

| | | | |
|---|---|---|---|
| 4,114,669 A | | 9/1978 | Bishop |
| 5,421,626 A | * | 6/1995 | Glachet .................... F16J 13/18 |
| | | | 292/241 |

(Continued)

FOREIGN PATENT DOCUMENTS

| | | |
|---|---|---|
| EP | 2111210 B1 | 11/2013 |
| EP | 2534052 B1 | 6/2014 |

(Continued)

OTHER PUBLICATIONS

International Preliminary Report on Patentability (and English Translation) for International Application No. PCT/FR2017/000141 dated Jan. 22, 2019.

(Continued)

*Primary Examiner* — Ariana Zimbouski
(74) *Attorney, Agent, or Firm* — Heslin Rothenberg Farley and Mesiti PC; Nicholas Mesiti

(57) ABSTRACT

The invention relates to a biopharmaceutical container comprising: a connector to be secured to a chamber connector; a bag serving as a receptacle, one part of which is secured to the connector; and a flexible tube tucked inside the bag, which tube can extend out from the bag through the connector. The biopharmaceutical container, wherein: the tube forms part of the bag, the tube is a neck of reduced size extending from the body of the bag, and the aforementioned part of the bag that is secured to the connector is a fold in the wall of the bag, said wall of the bag forming the body of the bag on one side of the fold and the tube on the other side of the fold.

33 Claims, 10 Drawing Sheets

(51) Int. Cl.
*A61J 1/14* (2023.01)
*A61M 39/10* (2006.01)

(56) References Cited

U.S. PATENT DOCUMENTS

| | | | | |
|---|---|---|---|---|
| 5,853,207 | A * | 12/1998 | Saint Martin | B01L 1/02 |
| | | | | 292/256.6 |
| 6,068,031 | A * | 5/2000 | Lataix | B65B 55/00 |
| | | | | 141/346 |
| 2012/0037633 | A1* | 2/2012 | Bernard | B65D 88/54 |
| | | | | 220/379 |
| 2013/0281964 | A1 | 10/2013 | Kugelmann et al. | |
| 2015/0330541 | A1* | 11/2015 | McCoy | F16L 47/02 |
| | | | | 285/288.1 |

FOREIGN PATENT DOCUMENTS

| | | | |
|---|---|---|---|
| FR | 2956092 | B1 | 2/2012 |
| WO | 2015098920 | A1 | 7/2015 |

OTHER PUBLICATIONS

Preliminary Search Report for French Priority Application No. 1670399 dated Mar. 20, 2017.
Office Action for European Patent Application No. 17751789.3 dated Oct. 21, 2020.
International Search Report (and English translation) and Written Opinion of the International Searching Authority for PCT/FR2017/000141 dated Dec. 7, 2017.

* cited by examiner

BIOPHARMACEUTICAL CONTAINER, BIOPHARMACEUTICAL CONTAINER BAG, AND METHOD FOR THE PRODUCTION AND USE OF SAID BIOPHARMACEUTICAL CONTAINER

CROSS REFERENCE TO RELATED APPLICATIONS

This application is a national stage filing under section 371 of International Application No. PCT/FR2017/000141, filed on Jul. 12, 2017, and published on Jan. 25, 2018 as WO 2018/015618 A1 which claims priority to French Patent Application No. 1670399, filed on Jul. 22, 2016, the entire disclosure of these applications being hereby incorporated herein by reference.

FIELD OF THE INVENTION

The invention relates to the field of biopharmaceutical containers, biopharmaceutical container bags, as well as methods for producing and using biopharmaceutical containers. The invention can also be applied to the steps of final filling of biopharmaceutical bags under aseptic conditions, including for a filling of biopharmaceutical fluid as described, for example, in patent EP 2534052B1 incorporated by reference.

BACKGROUND OF THE INVENTION

Biopharmaceutical containers are filled with a biopharmaceutical content, in particular of solid or liquid biopharmaceutical material or biopharmaceutical product type. This biopharmaceutical content, often sterile or sterilized, for example sterilized by gamma irradiations or by vapor, will usually be transferred into an often-sterile biopharmaceutical chamber, for example an isolator, to be stored there or to carry out a step of producing a biopharmaceutical product or to proceed with the final filling of this product. The transfer between biopharmaceutical container and biopharmaceutical chamber is a difficult operation during which the biopharmaceutical content can be contaminated, simply by the often, non-sterile outside environment. The structure of the biopharmaceutical container and the corresponding structure of the biopharmaceutical chamber are determined on the one hand to eradicate, minimize or at least reduce this risk of contamination, and on the other hand, to facilitate the transfer of the content from the container to the chamber.

A first type of biopharmaceutical container is known, in particular described in connection with FIG. 1, wherein the container bag is welded to the connector of the container. However, this container could be optimized, both with respect to the safety of the transfer and of the connected risk of contamination, as well as with respect to the facility and to the fluidity of the transfer of the content from the container to the chamber.

According to the invention, it would be about improving the protection of the critical zone, which is often a ring for passing between container and chamber, and which is a sensitive zone by which contaminant agents from the outside could be introduced preferably to be located in the communication space between container and chamber, over the passage of the transfer of the content from the container to the chamber. It is also about improving the fluidity of the transfer of the content from the container to the chamber, by channeling, even by guiding this transfer, particularly at the communication space between container and chamber.

A second type of biopharmaceutical container is known, in particular described in connection with FIG. 3, wherein the bag of the container is assembled with a protective interference fit protective sleeve, i.e. using an interference fit ring. This container has the interest, with respect to the first type of biopharmaceutical container, both for an improvement of the safety of the transfer, and for a decrease of the connected risk of contamination, as well as an improvement of the facility and of the fluidity of the transfer of the content from the container to the chamber. However, this container is subjected to a certain structure and production complexity.

According to the invention, it would be about simplifying the structure and the production of the container, while making it possible for it to continue to ensure, on the one hand, the protection of the critical zone for passing between container and chamber, by which contaminant agents from the outside could be introduced in the communication space between container and chamber, contaminating or risking contaminating the content during the transfer thereof, and on the other hand, the fluidity of the transfer of the content from the container to the chamber, by channeling or by guiding this transfer, in particular in the communication space between container and chamber.

SUMMARY OF THE INVENTION

The aim of the present invention is to provide a biopharmaceutical container at least partially overcoming the abovementioned disadvantages.

More specifically, the invention aims to provide a biopharmaceutical container having a simplification of structure and of production with respect to the second type of container, while having an improvement in safety of transfer with respect to the risk of contamination and an improvement of facility of transfer with respect to the first type of container.

Preferably, the invention aims to provide a biopharmaceutical container having a simplification of structure and of production comparable to that of the first type of container, while having an improvement in safety of transfer with respect to the risk of contamination and an improvement of facility of transfer comparable to that of the second type of container.

Preferably, the invention proposes to continue ensuring on the one hand, the protection of the critical zone for passing between container and chamber, comprising a specific risk of contamination, and on the other hand, the fluidity of the transfer of the content from the container to the chamber by channeling and/or guiding this transfer, while simplifying the structure and the production of the container, on the one hand by decreasing the number of components necessary to produce the container and/or on the other hand, by decreasing the number of steps for producing the container, it all possibly by also facilitating the use of the container to carry out the transfer of the content thereof The simplification of the structure and/or of the production of the container, while keeping the safety properties thereof against the risk of contamination and/or facilitation of the transfer of the content thereof, which are identical, similar or comparable, leads to equal or comparable quality, a substantially decrease of the cost thereof.

To this end, the present invention proposes a biopharmaceutical container, comprising: a connector to be secured to a chamber connector, a bag, serving as a receptacle, one part of which is secured to the connector, a flexible sleeve tucked inside the bag and can be unrolled out from the bag through the connector, characterized in that: the sleeve forms part of the bag, the sleeve is a neck of reduced size extending from the body of the bag, said bag part secured to the connector is a fold of the wall of the bag, the wall of the bag forms, on the one hand, the body of the bag on one side of the fold, and on the other hand, the sleeve on the other side of the fold. The connector in question, without more precision, in the biopharmaceutical container just described, is of course the connector of the container, except for when it is mentioned explicitly that it is a chamber connector.

This container is a product practically finalized during the method for producing the container.

The sleeve forms part of the bag. The sleeve and the bag are made of the same material, or at least one part of the sleeve and one part of the bag are made of the same material. The sleeve and the bag are only one single element, produced from one single holding, and not two elements produced separately then assembled to one another.

Preferably, the part of the bag secured to the connector is a part of the bag secured around the connector; this part of the bag secured to the connector can also be a part of the bag secured to the inside of the connector, or also to the edge of the connector.

According to preferable embodiments, the flexible sleeve has been directly integrated in the design of the wall of the bag. The flexible sleeve and the remainder of the body of the bag are thus one single and same part constituting the wall of the bag, extending from the bottom of the bag to the open end of the bag.

To this end, the present invention also proposes a biopharmaceutical container bag, comprising: a bag body serving as a receptacle, a part of the bag to be secured to a connector of the container, characterized in that it also comprises: a flexible sleeve, which is tucked inside the body of the bag and can be unrolled out from the body of the bag through the part of the bag to be secured to a connector of the container, which forms part of the bag, and which is a neck of reduced size extending from the body of the bag, and in that: the part of the bag to be secured to a connector of the container is a fold of the wall of the bag, the wall of the bag forms, on the one hand, the body of the bag on one side of the fold and on the other hand, the sleeve on the other side of the fold.

This bag is an intermediate product during the method for producing the container.

To this end, the present invention also proposes a biopharmaceutical container bag, comprising: a bag body serving as a receptacle, characterized in that it also comprises: a neck of reduced size, which extends from the body of the bag, which is to be a flexible protective sleeve for transferring the content of the bag, and which forms part of the bag.

This bag is an initial product during the method for producing the container.

To this end, the present invention also proposes a method for using a biopharmaceutical container according to the invention, characterized in that it comprises: a step of securing the container against an opening of a chamber, a step of unrolling the flexible sleeve outside of the body of the bag through the connector and through the opening of the chamber, a step of transferring the content from the container to the chamber through the unrolled sleeve. Preferably, between the securing step and the unrolling step, a simultaneous opening step is carried out, on the one hand from the doors of the biopharmaceutical container and on the other hand, from the doors of the chamber.

Preferably, between the securing step and the unrolling step, a step of opening the connector of the bag and of the chamber, making it possible for a connection of the inner, sterile spaces of the bag and of the chamber, after the transfer step, successively a step of retracting the flexible sleeve, a step of closing the connector of the bag and of the chamber, and a step of disconnecting from the container and from the chamber.

To this end, the present invention also proposes a method for using a biopharmaceutical container according to the invention, characterized in that it comprises: a step of securing the container against an opening of a chamber, a step of unrolling the flexible sleeve outside of the body of the bag through the connector and through the opening of the chamber, a step of transferring the used content from the chamber to the container through the unrolled sleeve.

This use method is a method of using a container according to the invention.

To this end, the present invention finally proposes a method for producing a biopharmaceutical container, comprising: a step of producing a bag comprising a bag body extended by a neck of reduced size, a step of tucking the neck inside the body of the bag, forming a fold in the wall of the bag between the body of the bag and the neck of the bag, a step of securing the fold to a connector to be connected to a chamber.

This production method is a method for producing a container according to the invention.

According to another aim of the invention, a biopharmaceutical container is also provided, comprising: a connector to be secured to a chamber connector, a bag, serving as a receptacle, one part of which is secured to the connector, a flexible sleeve tucked inside the bag and can be unrolled out from the bag through the connector, characterized in that: the sleeve forms part of the bag, the sleeve extends from the body of the bag, the sleeve having the same diameter or the same size as the body, this same diameter or this same size corresponding to the greatest dimension of the sleeve in a section being between 100 mm and 300 mm, preferably between 150 mm and 250 mm, even more preferably between 190 mm and 210 mm, said bag part secured to the connector is a fold of the wall of the bag, the wall of the bag forms, on the one hand, the body of the bag on one side of the fold, and on the other hand, the sleeve on the other side of the fold.

For increased sleeve sizes, corresponding to comparable sizes of the chamber door, the body of the bag can have a size equal to that of the sleeve. In this manner, the method for producing the bag including a body and a sleeve of the same size is simpler, since all of the bag, body and sleeve, is presented by a bag with a section of constant size, has a specific interest for a certain range of sizes corresponding to a certain range of sizes of chamber door. The bag being preferably cylindrical with a circular straight section, the range of corresponding diameters corresponds to 100-300 mm, preferably 150-250 mm, even more preferably 190-210 mm, for example 200 mm. The bag can have a straight section different from a circular straight section, for example, rectangular or square.

According to preferred embodiments, the invention comprises one or more of the following characteristics which can be used separately or in partial combination with one another, or in total combination with one another, with one or other of the aims of the invention presented above.

Preferably, said part of the bag secured to the connector is a part of the bag secured around the connector.

Thus, the fold is more solidly secured to the connector, in particular during the extension of the sleeve through the connector, as when the sleeve is unrolled by pulling on the fold, it rather tends to continue tightening the fold around the connector, rather than loosening it towards the inside of the connector, which could be the case if the fold was secured to the inner perimeter of the connector.

Alternatively, said part of the bag secured to the connector is a part of the bag secured to the inner perimeter of the connector.

Preferably, the fold of the wall of the bag comprises two bag wall portions folded onto one another, without free space between them, these two portions being advantageously secured against one another, these two portions being more advantageously welded against one another.

Thus, this sensitive connection zone between the wall of the bag and the connector, not only as a reinforcement zone thanks to the two layers, secured to one another, layers which are already the fold of one same wall, therefore secured to one another and which are thus even better secured to one another.

Preferably, the fold of the wall of the bag is secured to the connector, an overmolding being arranged between the connector and the fold, the fold being advantageously welded to the overmolding.

Thus, the material of the connector, rather a rigid material, has no need to have weld compatibility with the material of the bag, rather a flexible material. The overmolding having a notable thickness can be easily overmolded to the connector, despite the non-compatible weld materials. The overmolding will be selected from a compatible material, and even easily compatible, by welding, with the material of the bag.

Preferably, the overmolding comprises a cavity of which the inner shape molds the outer shape of a protuberance of the outer wall of the connector.

Thus, the solidity of the attachment between the overmolding, on the one hand, and the connector, on the other hand, is increased.

Preferably, the inside of the container is sterile.

This makes the invention all the more useful than the risk of contamination during the transfer of the content from the container to the chamber is critical and must absolutely be avoided.

Preferably, the bag is made of flexible plastic, preferably made of non-elastic plastic. The material used is, for example, a thermoplastic material which will be used with a thickness sufficiently fine to give the flexibility required.

In an alternative, the bag can be made of flexible and relatively elastic plastic to preserve the integrity of the container.

Thus, the bag is easy to produce and to use, in particular during the filling thereof by a content and during the transfer of the content thereof. The bag preferably avoids the risks of weakening, connected to an excessive elastic deformation, either starting to break, or making the plastic material more porous to the contaminant agents.

Preferably, the bag has a symmetry of revolution, or the part of the bag configured to be welded to the connector has a symmetry of revolution.

Thus, the bag is easier to produce and to use.

Several types of designs of bags can be considered. In a first design type, a two-dimensional bag is extruded. In a second design type, a two-dimensional bag is assembled. In a third design type, a three-dimensional bag is produced in a general parallelepipedal shape.

Preferably, the container is filled with biopharmaceutical materials to transfer into a chamber. This biopharmaceutical material can be, for example, packaging material, syringe stoppers, biopharmaceutical products, medications, or sterilized tools used for operations in the biopharmaceutical field, as well as final receptacles, or also single-use products for the transfer of fluid.

Preferably, the connector has a diameter of between 80 mm and 300 mm, preferably between 100 mm and 210 mm or the connector has a rectangular shape with a diagonal length of between 100 mm and 350 mm.

Thus, the relatively small size of the communication space between container and chamber makes the invention all the more useful, as this improves the battle against the risk of contamination and the facility of the transfer of the content of the container to the chamber, two aspect, all the more sensitive even all the more critical than this communication space is confined.

Preferably, in a biopharmaceutical container bag in the finalized shape thereof, the sleeve is only tucked over a part of the length thereof, advantageously over a part of between one third and two thirds of the length thereof, even more advantageously over a part equaling around half of the length thereof.

Preferably, the sleeve has a length which is between 100 mm and 900 mm, preferably between 300 mm and 900 mm, and even more preferably, between 600 mm and 900 mm.

Thus, on the one hand, it is easier to only tuck the sleeve over a part of the length thereof during the production of the container, and on the other hand, it is also easier to arranged one part of the untucked sleeve to unroll the sleeve more easily through the connector during the use of the container.

Alternatively, the sleeve cannot be tucked, but be for example left flat inside the container, or also be folded in a Z-shape at the connector.

Preferably, in the biopharmaceutical container bag, the neck comprises a visual mark, representative of the position limiting the tucking of the neck inside the body of the bag. This visual mark is used as a poka-yoke making it possible to see the stop position desired for the tucking. This very simple poka-yoke simplifies and also facilitates the method for producing the bag and therefore the container.

Preferably, this visual mark is the end of a length of additional weld along the bag, the start of this length of additional weld along the bag cooperating with the end of the neck of the bag adjoining the narrowing of the bag. Thus, this visual mark has the following advantages: first, it remains visible all the time, then, it can be made during the weld steps during the method for producing the bag, and not during an additional, distinct step of the method for producing the bag, then it does not require ink nor color, still potentially likely to be diffused through the wall of the bag and to contaminate the sterile or fragile content of the bag.

This aspect could also be used by itself, independently of all or some of the remainder of the container according to the invention. Another aim of the invention is, in this case, a biopharmaceutical container bag, comprising: a bag body serving as a receptacle, a part of the bag configured to be secured to a connector of the container, characterized in that it also comprises: a flexible sleeve, which is tucked inside the body of the bag and can be unrolled out from the body of the bag through the part of the bag configured to be secured to a connector of the container, which is a neck of reduced size extending the body of the bag, and in that: the neck comprises a visual mark representative of the position limiting the tucking of the neck inside the body of the bag, the neck comprises at least one longitudinal weld delimiting the neck by extending all along the neck, the neck comprises at least one additional weld extending along only one part of this longitudinal weld, the end of this additional weld, situated on the side of the opening of the neck, constituting said visual mark.

Preferably, the length of the additional weld of which the end materializes the visual mark, substantially corresponds to the width of the ring, circular or not, constituting the connector.

Preferably, in the biopharmaceutical container bag, the free end of the sleeve or of the neck is open.

Thus, the sleeve will be ready to be used as soon as it is unrolled, without requiring an additional step of opening an orifice at the end of the sleeve to make it possible for the passing of the content during the transfer thereof from the container to the chamber. Moreover, the fact that the sleeve is tucked inside the bag and that the passage of the connector is closed by another element, makes it possible for the end of the sleeve to be open without any notable disadvantage for the sterility of the container.

Preferably, in the biopharmaceutical container bag, the bag comprises a progressive narrowing of the body of the bag before the sleeve or the neck of the bag.

This narrowing, advantageously as a funnel, is preferably conical, increases the fluidity of the transfer of the content from the container to the chamber.

Preferably, in the biopharmaceutical container bag, the sleeve or the neck has a section at least 4 times smaller than the section of the body of the bag, advantageously at least 10 times smaller.

Thus, the fluidity of the transfer of the content from the container to the chamber remains guaranteed, even when the container has a significant body section, which increases the capacity thereof, and when simultaneously the opening of the chamber has a relatively small section, which decreases the volume and the complexity of the door closing this opening of the chamber in absence of transfer coming from a container.

Preferably, in the biopharmaceutical container bag, the sleeve or the neck has a length equaling at least one tenth of the length of the body of the bag, advantageously at least one quarter.

Thus, the sleeve makes it possible for a channeling and even a guiding through the whole communication space situated between container and chamber, so as to release the content of the container only inside the chamber, where it can be more easily handled by a user or by a robot.

Preferably, the method for producing a biopharmaceutical container also comprises: a step of closing the connector by a door so as to seal the container at the connector, a step of filling the container with content, a step of closing the bag bottom so as to seal the container at the bag bottom, a step of sterilizing the container filled with content. Thus, the door is closed before filling the container, and the bottom of the bag remains open: the bag is filled, and only then the bottom of the bag will thus be closed.

Alternatively, the method for producing a biopharmaceutical container also comprises: a step of filling the container with content, a step of closing the connector by a door to as to seal the container at the connector, a step of sterilizing the container filled with content.

Thus, a filled container, closed and sterile, can be easily stored and transported, before being led into contact with the chamber, to discharge the sterile content thereof into it.

According to another alternative, the bag comprises two connectors, one at each end, the bag is delivered sterile. Then, a sterilization of material is done in an autoclave provided with an autoclave connector of the type of a chamber or isolator connector. Then, the material is transferred from the autoclave into the bag via the first connector of the bag. Finally, the second connector of the bag will be used to produce the connection between the bag and the isolator.

Preferably, in the production step, the bag is extruded or assembled, between the tucking step and the securing step, one or more possible folding steps.

Other characteristics and advantages of the invention will appear upon reading the following description of a preferred embodiment of the invention, given as an example and in reference to the appended drawings.

LIST OF REFERENCES IN THE FIGURES

1/ biopharmaceutical container bag
2/ biopharmaceutical container bag body
3/ biopharmaceutical container bag narrowing
4/ biopharmaceutical container bag neck
5/ neck opening
6/ biopharmaceutical container bag bottom
7/ biopharmaceutical container bag wall fold
8/ tucked part of the neck
9/ end of the neck
10/ biopharmaceutical container bag sleeve
11/ biopharmaceutical container door
12/ overmolding
13/ cavity of the overmolding
14/ connector of the biopharmaceutical container
15/ securing surface of the connector
16/ protuberance of the connector
17/ connector rim
18/ communication space configured to be closed by the door
19/ separate sleeve
20/ interference fit ring
21/ chamber door joint
22/ biopharmaceutical container door cover
23/ biopharmaceutical container door metal plate
24/ overmolding perimeter
25/ chamber door
26/ chamber door arm
27/ chamber door arm rotating axis
28/ anchoring base of the rotating axis
29/ wall of the chamber
30/ chamber
31/ biopharmaceutical container
32/ wall of the bag
33/ opening of the chamber
34/ visual mark
35/ weld
36/ additional weld of the visual mark
37/ lug
38/ hole
39/ color coding
40/ bag side fold
d/ diameter of the open end of the neck
D/ diameter of the end of the narrowing secured to the connector
L/ sleeve length
l/ additional weld length
α/ narrowing angle
L1/ length of the body of the bag
L2/ width of the body of the bag
h/ height of the bag side folds

DETAILED DESCRIPTION OF THE INVENTION

Figure 1:
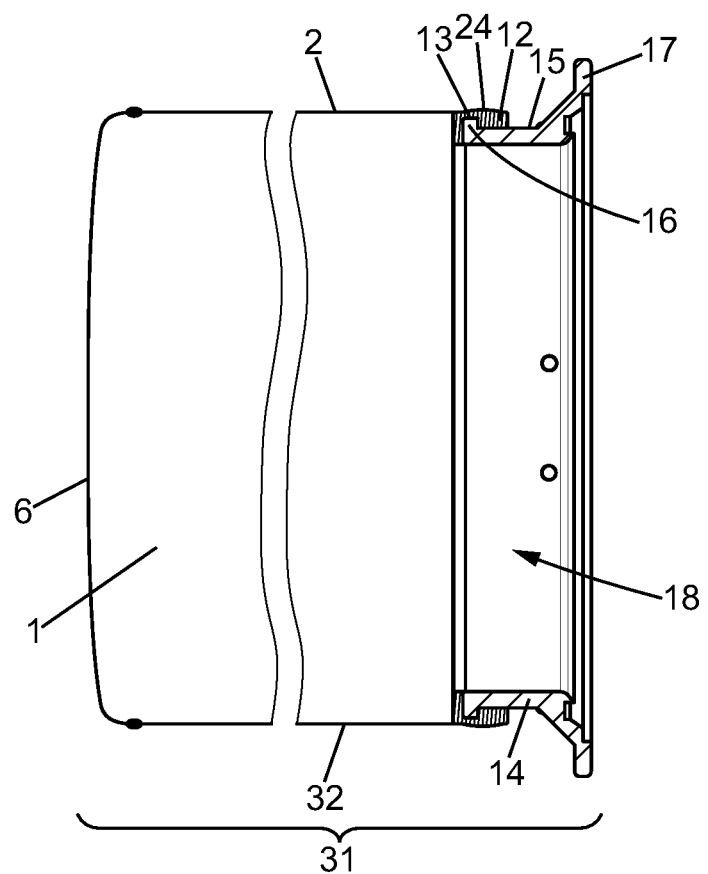
FIG. 1 schematically represents a cross-sectional view of an example of first type of biopharmaceutical container welded with no sleeve.

FIG. 1 schematically represents a cross-sectional view of an example of first type of biopharmaceutical container welded with no sleeve.

A container 31 comprises two main parts which are a flexible bag 1 but not elastic and a rigid connector 14, the bag 1 and the connector 14 both being cylindrical of revolution, the bag 1 being secured around the connector 14 by way of an overmolding 12 situated between both. The bag 1, the connector 14 and the overmolding 12, are cylindrical with a symmetry of revolution.

The connector 14 comprises a rim 17, a securing surface 15 having a protuberance 16. At the center of the connector 14 which is annular is located the communication space 18 situated between container 31 and chamber, not represented in this FIG. 1, to be clear, but represented in FIG. 2.

The overmolding 12 comprises a perimeter 24 and a cavity 13. The overmolding 12 is overmolded annularly on the securing surface 15 of the connector 14, the cavity 13 of the overmolding 12 being slotted into the protuberance 16 of the connector 14.

The bag 1 comprises a bottom 6, a cylindrical wall 32 of revolution extending along a body 2. The body 2 of the bag 1 is welded annularly over the perimeter 24 of the overmolding 12.

All that is needed is a blocking element to close the communication space 18 such that the container 31 is finalized. Either the container 31 is filled first then the blocking element is then implemented, or the blocking element is first implemented, then the container 31 is then filled. The bag 1 is closed by the bottom 6 thereof. More specifically, the bag 1 is for example tubular or formed of two sheets of film apposed on one another in the longitudinal extension of one another. To weld the bottom 6 of the bag 1, the end of the bag 1 on the side of the bottom 6 is flattened, and a weld is done through the width.

Figure 2:
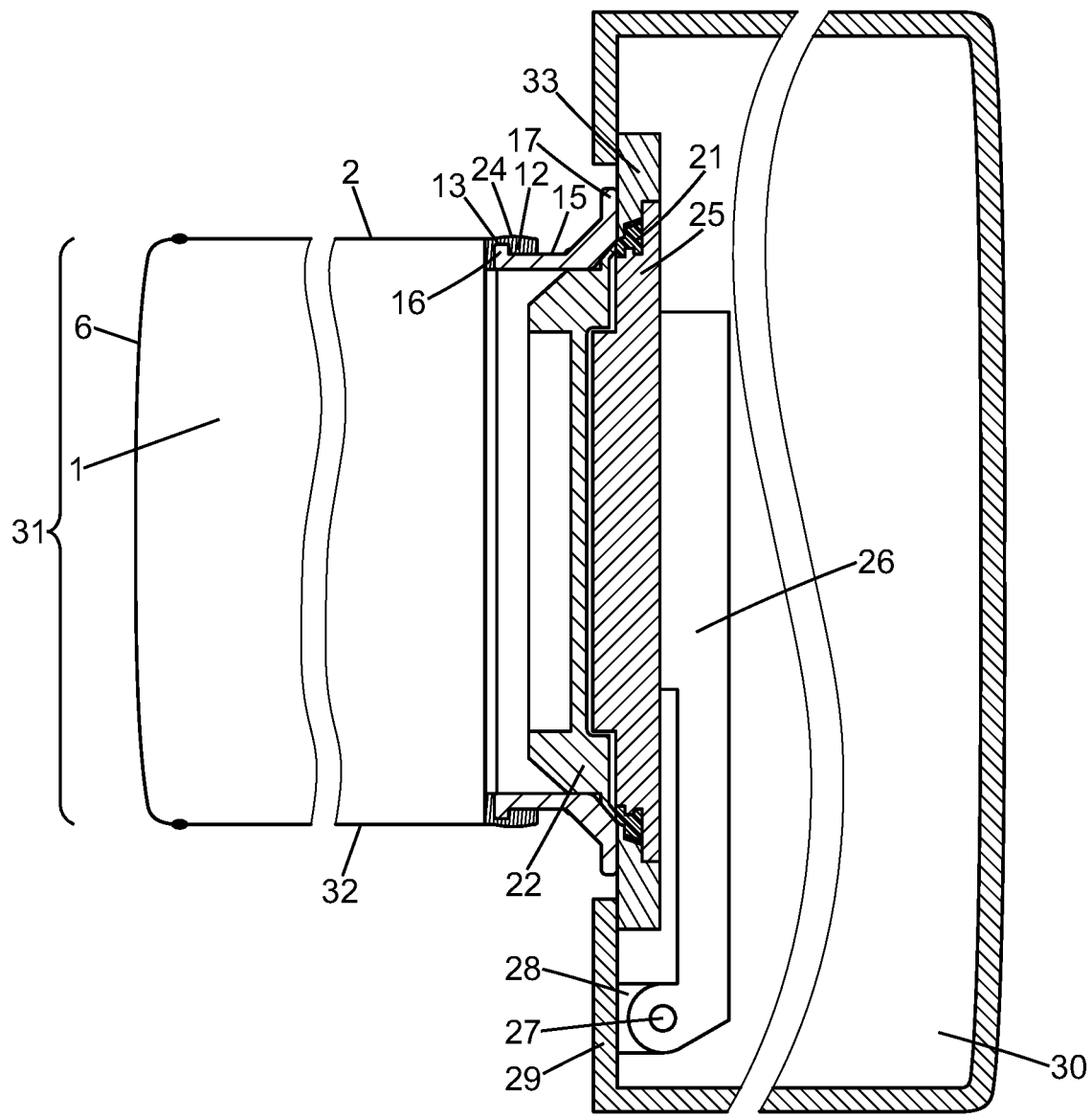
FIG. 2 schematically represents a cross-sectional view of an example of assembling the chamber and biopharmaceutical container using a first type of biopharmaceutical container welded with no sleeve.

FIG. 2 schematically represents a cross-sectional view of an example of assembling a chamber and a biopharmaceutical container using a first type of biopharmaceutical container welded with no sleeve.

The container 31 of FIG. 1 is represented secured on the opening 33 of the chamber 30, or more specifically over the perimeter of the opening 33 of the chamber 30. This opening 33 is closed by a door 25 of the chamber 30, a joint 21 being arranged between the perimeter of the opening 33 of the door 25. This opening 33, or more specifically this perimeter of the opening 33, plays the role of chamber connector 30, and this is on this chamber 30 connector 33 which the connector 14 of the container 31 is secured. A door cover 22 of the container 31 closes this container 31 and is secured against the door 25 of the chamber 30. An arm 26 is secured to the door 25 to tilt in the chamber 30, the secured assembly constituted by, on the one hand, the door of the container 31 of which the cover 22 is only represented and, on the other hand, the door 25 of the chamber 30. This tilting is made about a rotating axis 27 supported by an anchoring base 28 to the wall 29 of the chamber 30.

When the container 31 is secured against the opening 33 of the chamber 30, the secured assembly constituted by the cover 22 and the door 25, supported by the arm 26, tilts about the rotating axis 27, towards the inside of the chamber 30 leaving the central space of the connector 14 free, through which the content of the container 31 can be discharged into the chamber 30. Nothing protects the content of the container 31 during the transfer thereof into the chamber 30, at the time of the passing thereof by a sensitive ring situated at the joint 21 by which contaminant agents risk entering into the communication space between container 31 and chamber 30.#

Figure 3:
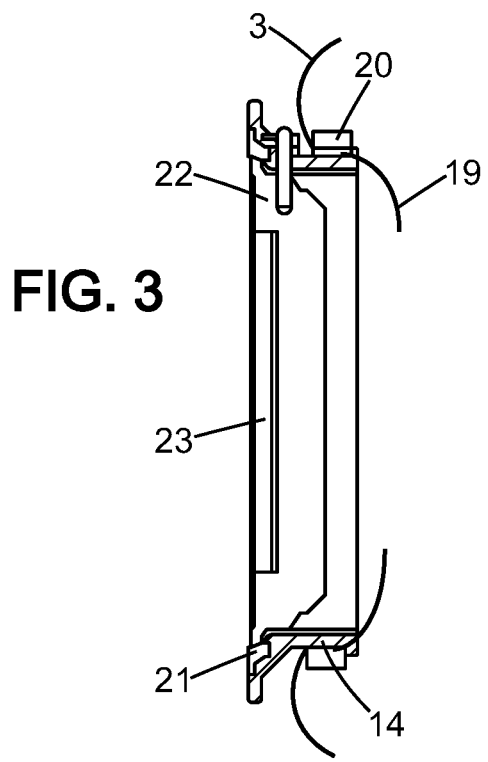
FIG. 3 schematically represents a cross-sectional view of an example of second type of biopharmaceutical container interference fitted with sleeve according to the prior art.

FIG. 3 schematically represents a cross-sectional view of an example of second type of biopharmaceutical container interference fitted with sleeve according to the prior art.

The door of the container comprises a metal plate 23 overmolded at the center of the cover 22. This metal plate 23 is magnetized and is situated on the outer side, therefore in the fresh air and therefore contaminated. This magnetized metal plate 23 flattens the connector 14 against the door of the chamber. When the doors of the container and of the chamber are unlocked, the door of the chamber brings with it the door of the container, the contaminated part thus being isolated from the sterile atmosphere of the chamber.

A protective sleeve 19 is secured to the connector 14 with the narrowing 3 of the container by interference fitting, i.e. by being tightened to the connector just like the narrowing 3 by an interference fit ring 20. This second type of container comprises numerous distinct parts, of which the sleeve part 19, returned with respect to the narrowing 3, and of which the interference fit ring 20. The production of this second type of container is relatively difficult and complex.

Figure 4:
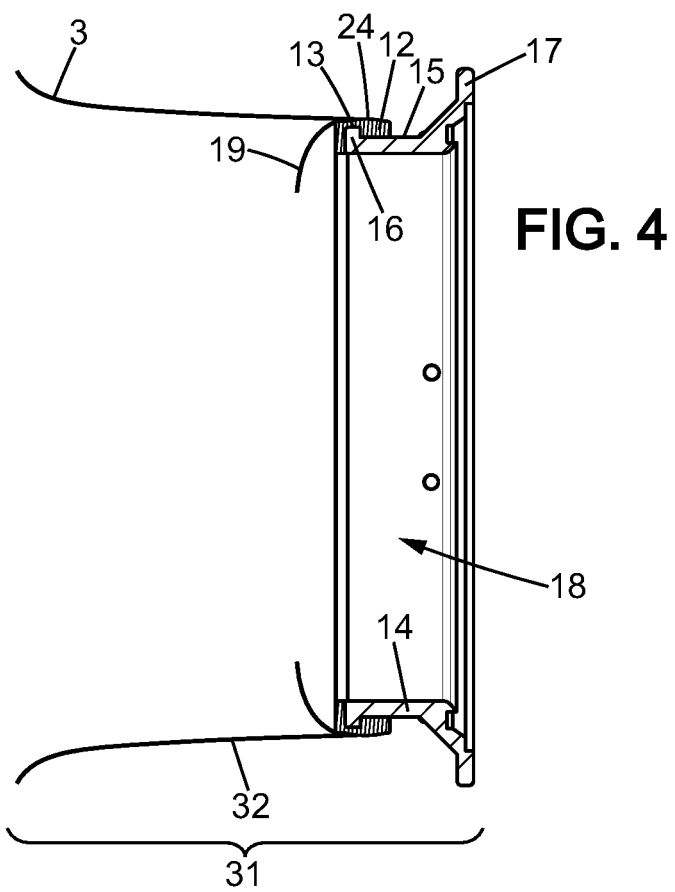
FIG. 4 schematically represents a cross-sectional view of an example of a third type of biopharmaceutical container welded with sleeve.

FIG. 4 schematically represents a cross-sectional view of an example of a third type of biopharmaceutical container welded with sleeve.

It can be imagined to improve the second type of container by replacing the interference fitting of the narrowing 3 and of the sleeve 19 returned onto the connector 14 by a weld, both of the narrowing 3 and of the sleeve 19 returned, not directly onto the connector 14, but onto an overmolding 12 for better weld compatibility. The returned sleeve 19 could be tucked inside the container 31. The production method would be simplified, as welding is simpler than interference fitting, and the number of parts used decreased, because of the removal of the ring 20. However, this third type of possible container, not yet known from the prior art, would all the same have two distinct parts, narrowing 3 and returned sleeve 19, to be welded together either directly to the connector 14, or by way of the overmolding 12, from where a certain remaining complexity that the invention has chosen to simplify, as keeping described and explained in connection with FIG. 5.

Figure 5:
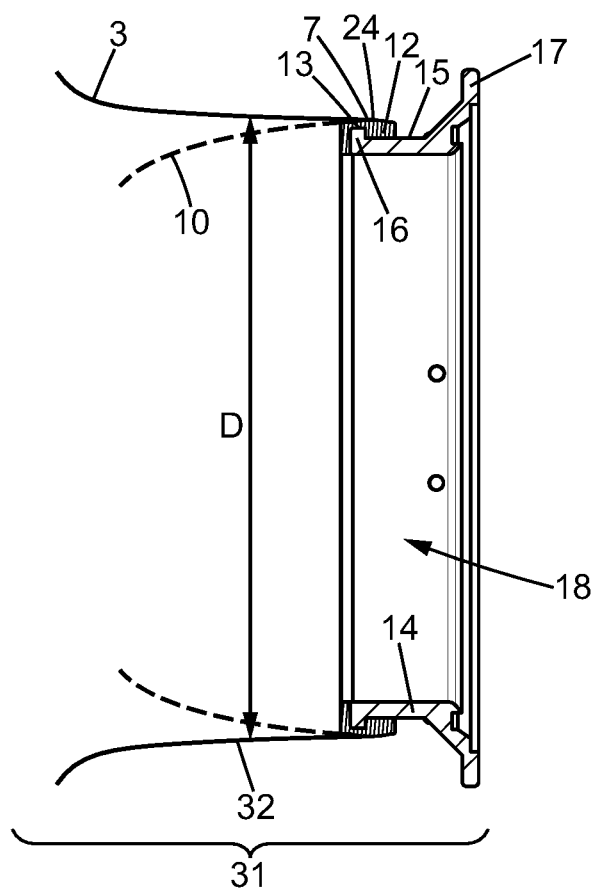
FIG. 5 schematically represents a cross-sectional view of an example of an embodiment of a biopharmaceutical container welded with sleeve according to the invention.

FIG. 5 schematically represents a cross-sectional view of an example of an embodiment of a biopharmaceutical container welded with sleeve according to the invention. The container 31 of FIG. 5 can be secured in the same manner as the container 31 of FIG. 1 to the chamber 30 of FIG. 2. The diameter D represents the diameter of the end of the narrowing 3 secured to the connector 14 at the time of coming to the overmolding 12. This diameter D is greater than the diameter d of the opening end of the neck 4.

A container 31 comprises two main parts which are a flexible bag 1, but not elastic, and a rigid connector 14, the bag 1 and the connector 14 both being cylindrical of revolution, the bag 1 being secured around the connector 14 by way of an overmolding 12 situated between both. The bag 1, the connector 14 and the overmolding 12, are cylindrical with a symmetry of revolution.

The connector 14 comprises a rim 17, a securing surface 15 having a protuberance 16. At the center of the connector 14 which is annular is located the communication space 18 situated between container 31 and chamber not represented in this FIG. 5, to be clear, but represented in FIG. 2.

The overmolding 12 comprises a perimeter 24 and a cavity 13. The overmolding 12 is overmolded annularly over the securing surface 15 of the connector 14, the cavity 13 of the overmolding 12 being slotted into the protuberance 16 of the connector 14.

The bag 1 comprises a bottom 6, a cylindrical wall 32 of revolution extending along a body 2 and a narrowing 3. In the wall 32 of the bag 1, a fold 7 is formed. On either side of this fold 7 of the wall 32 of the bag 1, being situated respectively, on the one hand, in the narrowing 3 of the bag 1 and, on the other hand, the sleeve 10 forming part of the bag 1 and constituting the extension of this wall 32 of the bag 1. The fold 7, formed of the superposition of both layers respectively constituted by the narrowing 3 and the integrated sleeve 10, is welded annularly over the perimeter 24 of the overmolding 12, such that the narrowing 3 is welded against the integrated sleeve 10 itself welded against the perimeter 24 of the overmolding 12.

All that is needed is a blocking element to close the communication space 18 such that the container 31 is finalized. Either the container 31 is filled first then the blocking element is then implemented, or the blocking element is first implemented, then the container 31 is then filled, and finally the bottom 6 is welded to the body 2 to close the bag 1 and therefore the container 31 instead of having been welded beforehand to the body 2.

In an alternative not represented in FIG. 5, the bag 1 can be, in particular, a bag suitable for the transfer of a fluid. In this case, a pipe having at the end thereof, a fluidic connector making it possible for an aseptic connection passes through, in a sterile manner, the wall 32 of the bag 1. This pipe can thus be inserted in a sterile manner into the chamber 30 to form a sterile line between, on the one hand, an end of the pipe, by which can be entered the biopharmaceutical content, and on the other hand, the chamber 30 until which this biopharmaceutical content can be conveyed.

Figure 6:
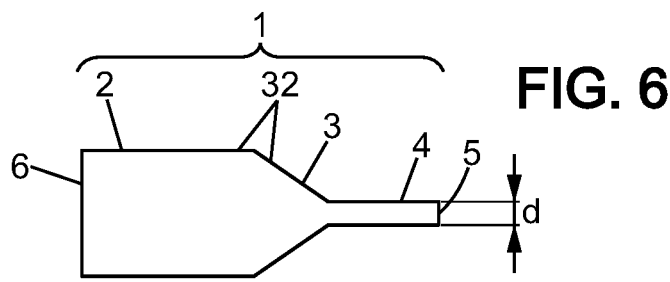
FIG. 6 schematically represents an example of a first step of a production method of an embodiment of a biopharmaceutical container welded with sleeve according to the invention, this container being represented in profile.

FIG. 6 schematically represents an example of a first step of a method for producing an embodiment of a biopharmaceutical container welded with sleeve according to the invention, this container being represented in profile.

A bag 1, in the form of plastic film, overall cylindrical of revolution, is produced in a first step. This bag 1 comprises a wall 32, extending between the bottom 6 of the bag 1 and the opening 5 of the neck 4, by surrounding the body 2, the narrowing 3 and the neck 4 of the bag 1. The bag 1 has an overall bottle shape, the diameter d of the opening 5 of the neck equaling for example 110 mm, even 200 mm. However, the wall 32, including the body 2, the narrowing 3 and the neck 4, is one single holding. The body 2 and the neck 4 have a cylindrical shape of revolution, while the narrowing 3 has a conical shape of revolution.

Figure 7:
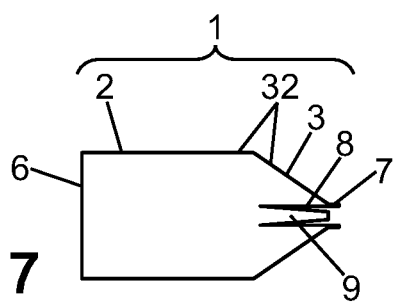
FIG. 7 schematically represents an example of a second step of a method for producing an embodiment of a biopharmaceutical container welded with sleeve according to the invention, this container being represented in profile.

FIG. 7 schematically represents an example of a second step of a method for producing an embodiment of a biopharmaceutical container welded with sleeve according to the invention, this container being represented in profile.

The neck 4 is tucked over half of the length 8 thereof, conserving the end 9 untucked, and forming a fold 7 between the part 8 and the narrowing 3.

Figure 8:
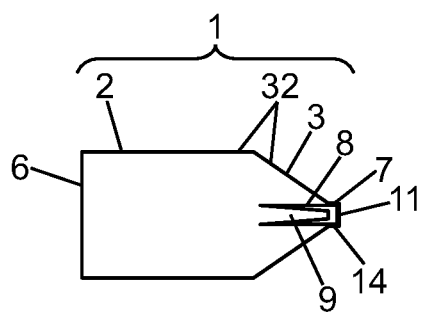
FIG. 8 schematically represents an example of a third step of a production method of an embodiment of a biopharmaceutical container welded with sleeve according to the invention, this container being represented in profile.

FIG. 8 schematically represents an example of a third step of a method for producing an embodiment of a biopharmaceutical container welded with sleeve according to the invention, this container being represented in profile.

The fold 7 is welded over the perimeter of the connector 14 at the center of which is placed a door 11 closing the container 31. The weld of the fold 7 is done, for example around 120° C., so as to make the wall 32 melt, but far from the melting point of the connector 14, which can be, for example, around 200° C. At the fold 7, the narrowing 3 is welded against the part 8 of the wall 32 itself welded on the connector 14, either directly or by way of an overmolding, not represented in FIG. 8, to be clear.

Figure 9:
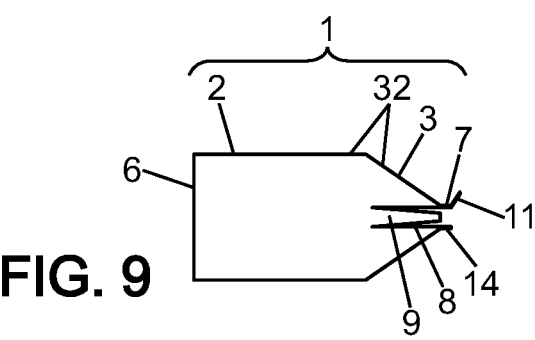
FIG. 9 schematically represents an example of a first step of a production method of an embodiment of a biopharmaceutical container welded with sleeve according to the invention, this container being represented in profile.

FIG. 9 schematically represents an example of a first step of a method for using an embodiment of a biopharmaceutical container welded with sleeve according to the invention, this container being represented in profile.

Once the third production step has ended in FIG. 8, the content of the container 31 having been added just before the closing by the door 11, the container 31 can be used. It is also possible to only weld the bottom 6, at the end of this third production step which ended in FIG. 8, once the door 11 is installed, and after having filled the container 31 through the bottom 6 thereof. Once the container 31 is secured against an opening of the chamber, not represented to be clear, the door 11 is open, making accessible, from the inside of the chamber, the end 9 of the integrated sleeve 10. The user or the robot, situated in the chamber only has to seize the end 9 and pull it towards the inside of the chamber (to the right in FIG. 9), to unroll this integrated sleeve 10 to the wall 32 of the bag 1.

Figure 10:
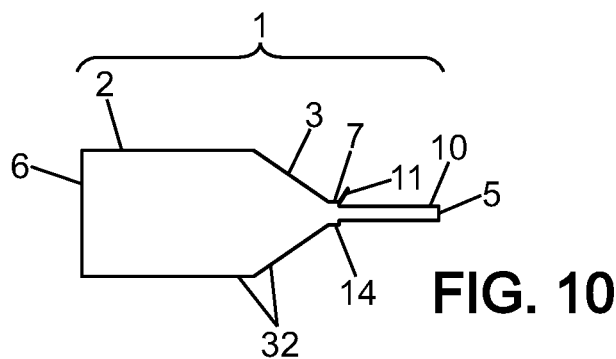
FIG. 10 schematically represents an example of a second step of a method for using an embodiment of a biopharmaceutical container welded with sleeve according to the invention, this container being represented in profile.

FIG. 10 schematically represents an example of a second step of a method for using an embodiment of a biopharmaceutical container welded with sleeve according to the invention, this container being represented in profile.

The integrated sleeve 10 has been unrolled. The content of the container 31, situated in the body 2, can pass into the narrowing 3, then by the integrated sleeve 10, thus passing through the communication space (not represented to be clear) situated between container 31 and chamber, to come away from the integrated sleeve 10 by the opening 5, to come to the inside of the chamber.

The production method, such as represented in FIGS. 6 to 8, will in particular be used to assemble a bag 1 of which the wall 32 is made of plastic film with a connector 14 made of polycarbonate (PC) or acrylonitrile butadiene styrene (ABS) or polyvinylidene fluoride (PVDF), or polybutylene terephthalate (PBT). Such materials for the connector 14 will be rigid and can support the locking forces against the door of the chamber, as well as resisting the different treatments associated with vapor sterilization (at temperatures less than 125° C.), gamma sterilization or ethylene oxide sterilization.

The plastic film of the wall 32 of the bag 1 can be, in particular, made of polyethylene (PE), high-density polyethylene (HDPE), or low-density polyethylene (LDPE).

The product of the overmolding 12 will thus be, for example, made of polyethylene (PE), high-density (HDPE) or in the form of thermoplastic elastomer (TPE), or can also be made of thermoplastic elastomer or of polypropylene or polyvinylidene fluoride (PVDF). The overmolding 12 will not melt with the increase of temperature when it is mounted on the connector 14 which will thus withstand the deformation thereof.

The weld of the plastic film of the fold 7 on the overmolding 12 resists gamma ray sterilization or vapor sterilization well.

To carry out the weld, the film of the wall 32 of the bag 1 and the overmolding 12 will begin melting almost at the same time therefore in temperature ranges close to around 120° C. (far from the weld temperatures selected for the connector 14 equaling rather around 200° C.).

The following options can in particular be considered, among which:
 the connector 14 is made of polyvinylidene fluoride (PVDF), and the overmolding 12 is made of high-density polyethylene (HDPE), or made of thermoplastic elastomer (TPE) or PBT or PMMA (polymethyl methacrylate),
 the connector 14 is made of polycarbonate (PC) and the overmolding 12 is made of high-density polyethylene (HDPE) or made of thermoplastic elastomer (TPE) or PBT or PMMA (polymethyl methacrylate),
 the connector 14 is made of acrylonitrile butadiene styrene (ABS) and the overmolding 12 is made of high-density polyethylene (HDPE) or made of thermoplastic elastomer (TPE) or PBT or PMMA (polymethyl polymethacrylate),
 the connector 14 is made of polybutylene terephthalate (PBT) and the overmolding 12 is made of high-density polyethylene (HDPE) or made of polyvinylidene fluoride (PVDF) or PBT (in particular for welding a bag made of copolyester) or PMMA (polymethyl methacrylate).

Figure 11:
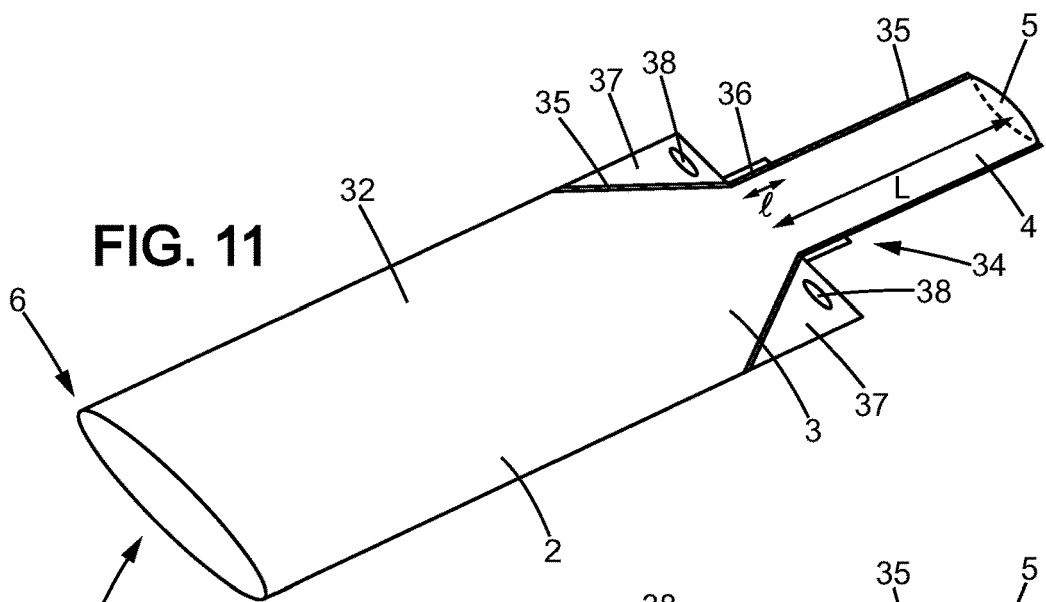
FIG. 11 represents a first example of type of method for producing a bag according to the invention, by extruding a plastic film.

FIG. 11 represents a first example of type of method for producing a bag according to the invention, by extruding a plastic film.

The bag 1, in the form of plastic film, overall cylindrical of revolution, comprises a wall 32, extending between the bottom 6 of the bag 1 and the opening 5 of the neck 4, by surrounding the body 2, the narrowing 3 and the neck 4 of the bag 1. The bag 1 has an overall bottle shape. The wall 32, including the body 2, the narrowing 3 and the neck 4, and of one single holding. The body 2 and the neck 4 have a cylindrical shape of revolution, while the narrowing 3 has a conical shape of revolution.

The wall 32 mainly comprises an extruded cylindrical film, constituting the body 2, the narrowing 3 and the neck 4 being delimited by welds 35. Outside of the inner space of the bag 1, delimited by the welds 35, are located two lugs 37 born with holes 38 making it possible to fasten the bag 1. At the end of the neck 4 situated on the side of the end of the small size of the narrowing 3, an additional weld 36 is produced, of length 1 equaling around 100 mm, which starts at the end of the narrowing 3 and which is ended at the visual mark 34; indeed, it is the end of the additional weld 36 which constitutes a physical excrescence materializing the visual mark 34. This visual mark 34 will be used to tuck the neck 4 inside the bag 1 during the final steps of producing the bag 1.

The plastic film is flexible, but not elastic. This film can be constituted of ether copolyester layers, the bag 1 being able to be sterilized by vapor and by γ (gamma) rays. This film can also be multilayer and thus be constituted of a succession of following layers: polyethylene (PE)/polyacrylate (PA)/polyethylene (PE), the bag 1 being able to be sterilized by γ rays.

Figure 12:
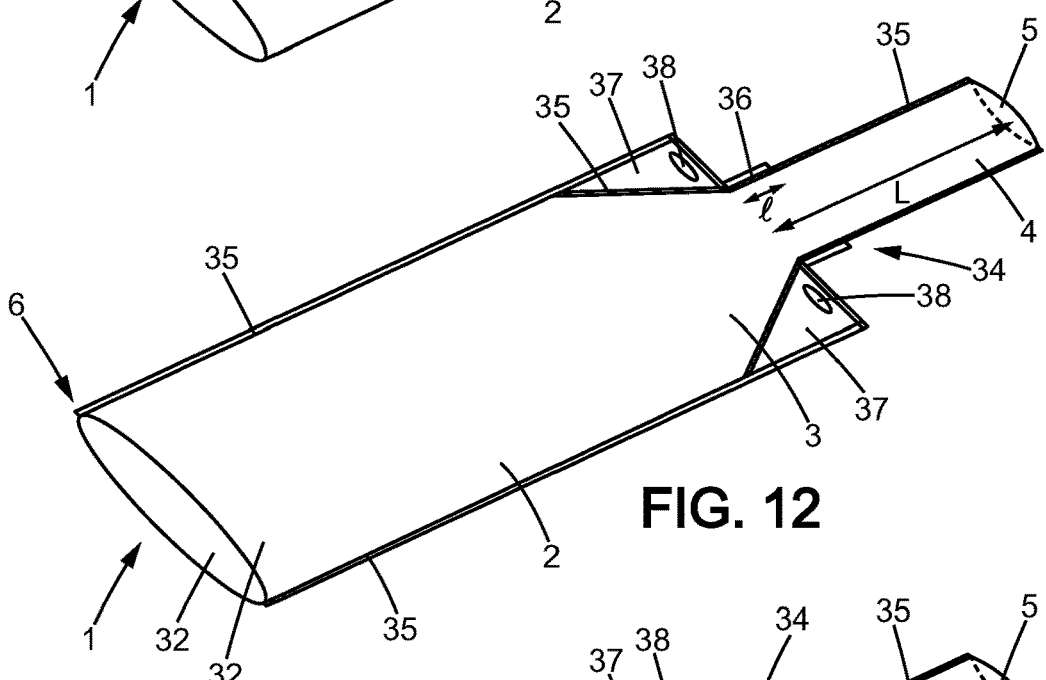
FIG. 12 represents a second example of type of method for producing a bag according to the invention, by welding two sheets of plastic film onto one another.

FIG. 12 represents a second example of type of method for producing a bag according to the invention, by welding two sheets of plastic film onto one another.

This second type of method for producing bags is distinguished from the first type of method for producing bags described above, also regarding the result, i.e. the bag obtained. Indeed, the welds 35, situated on each side of the narrowing 3, extending all along the body 2.

The plastic film is flexible, but not elastic. This film can be constituted of a high-density polyethylene (HDPE) layer. The whole or at least one part of one of the two films welded onto one another, for example half of the body 2 situated farther from the narrowing 3, can be constituted of a layer of interconnected high-density polyethylene (HDPE) fibers, the bag 1 thus being able to be sterilized by vapor. This film can also be constituted of a high-density polyethylene layer (HDPE). The whole or at least one part of one of the two films welded to one another, for example half of the body 2 situated farther from the narrowing 3, can be constituted of a PES (polyethylene sulfone) membrane, the bag 1 thus being able to be sterilized by vapor. This membrane can alternatively comprise a membrane made of polyethylene sulfone (PES) and flakes of polypropylene (PP) fibers coated with polyethylene (PE).

Figure 13:
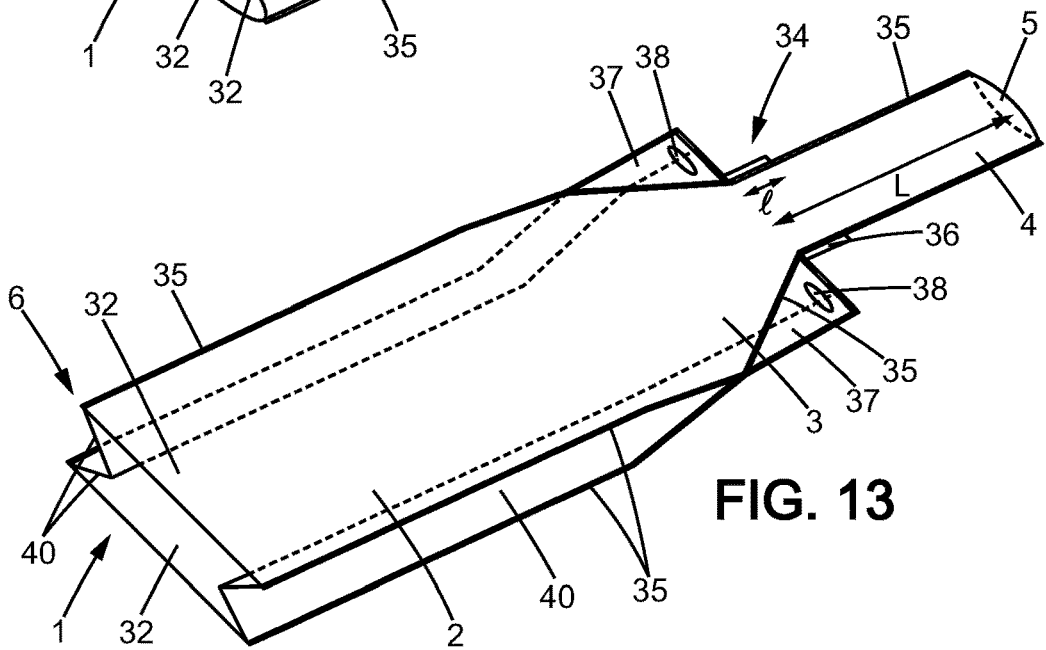
FIG. 13 represents a third example of type of method for producing a bag according to the invention, by welding two sheets of plastic film onto one another, with welding two side folds between the two plastic sheets.

FIG. 13 represents a third example of type of method for producing a bag according to the invention, by welding two sheets of plastic film onto one another, with welding of two side folds between the two plastic sheets.

This third type of method for producing bags is distinguished from the second type of method for producing bags described above, also regarding the result, i.e. the bag obtained. Indeed, the welds 35, situated on each side of the body are duplicated, because of the insertion, all along the body 2, of side folds 40 advantageously V-shaped. Once the sterilization is done, the welds 35 on each side of the bag 1 can be rewelded between each other two by two, such that the side folds 40 are thus fully inside the bag 1 and are no longer in direct contact with the outer medium to the bag 1.

The plastic film is flexible but not elastic. This film can be constituted of ether copolyester layers, the bag 1 being able to be sterilized by vapor and by Trays. This film can also be multilayer and be constituted of a succession of following layers: polyethylene (PE)/polyacrylate (PA)/polyethylene (PE), the bag 1 being able to be sterilized by Trays.

This film can also be constituted of a high-density polyethylene (HDPE) layer. The whole or at least one part of one of the two films welded to one another, for example half of the body 2 situated farther from the narrowing 3, can be constituted of a membrane made of PES, the bag 1 thus being able to be sterilized by vapor through this membrane made of PES. Preferably, the two films are constituted of a high-density polyethylene (HDPE) layer. The side folds 40 are thus constituted of a membrane made of PES, the bag 1 thus being able to be sterilized by vapor through this membrane. This membrane can alternatively comprise a membrane made of polyethylene sulfone (PES) and flakes of polypropylene (PP) fibers coated with polyethylene (PE).

This film can also be constituted of a high-density polyethylene (HDPE) layer. The whole or at least one part of one of the two films welded to one another, for example half of the body 2 situated farther from the narrowing 3, can be constituted of a layer of interconnected high-density polyethylene (HDPE) fibers, the bag 1 thus being able to be sterilized by vapor, through this layer of interconnected high-density polyethylene (HDPE) fibers. The side folds 40 are constituted of a layer of interconnected high-density polyethylene (HDPE) fibers, the bag 1 thus being able to be sterilized by vapor, through this layer of interconnected high-density polyethylene (HDPE) fibers.

Figure 14:
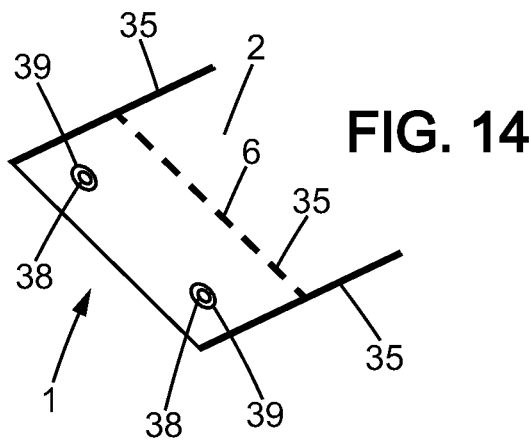
FIG. 14 represents an example of the bottom of a bag according to the invention.

FIG. 14 represents an example of the bottom of a bag according to the invention.

The bag 1, at the body 2, on the side of the bottom 6, has two longitudinal welds 35 delimiting the body 2, and a transverse weld 35 applied after filling the bag 1 with the content thereof, so as to constitute the bottom 6 of the bag 1. Beyond the bottom 6, two holes 38 are made to be able to fasten the bag 1 at the base. Colored rings 39 can constitute a color code making it possible to distinguish, with a simple glance, the type of bag 1 in question.

Figure 15:
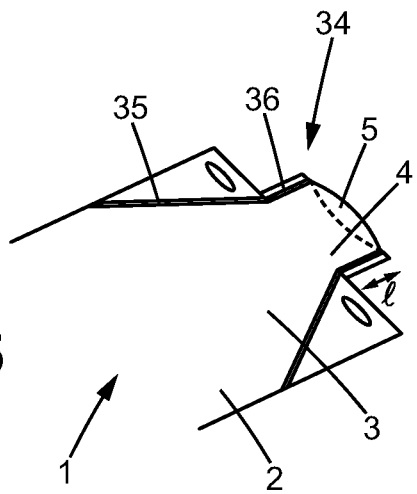
FIG. 15 represents a bag example according to the invention, having a short sleeve.

FIG. 15 represents a bag example according to the invention, having a short sleeve.

The bag 1 represented is a bag with a short neck 4, as this neck 4 only extends the narrowing 3 by a reduced length, here l equaling for example, around 100 mm. The additional weld 34 extends over the whole length of the short neck 4. The visual mark 34 is therefore situated at the open end 5 of the short neck 4.

Figure 16:
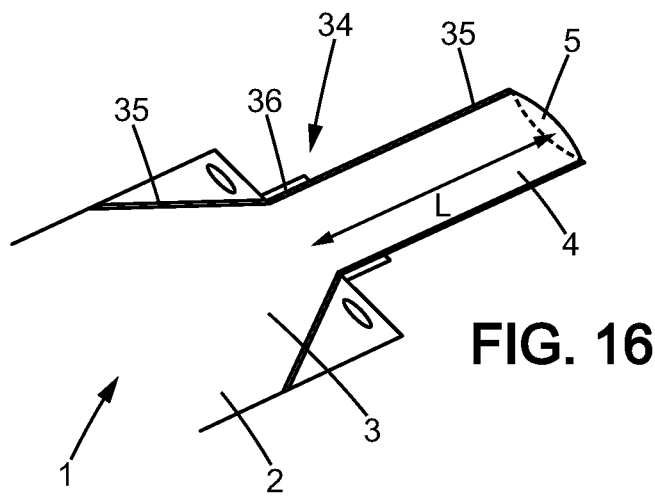
FIG. 16 represents another bag example according to the invention, having a long sleeve.

FIG. 16 represents another bag example according to the invention, having a long sleeve.

The bag 1 represented is a bag with a long neck 4, as this neck 4 extends the narrowing 3 by a significant length, here L equaling for example, around 900 mm. The additional weld 34 only extends over one part of the length of the long neck 4, namely over a length l equaling for example, 100 mm. The visual mark 34 is therefore situated far from the open end 5 of the long neck 4.

Figure 17:
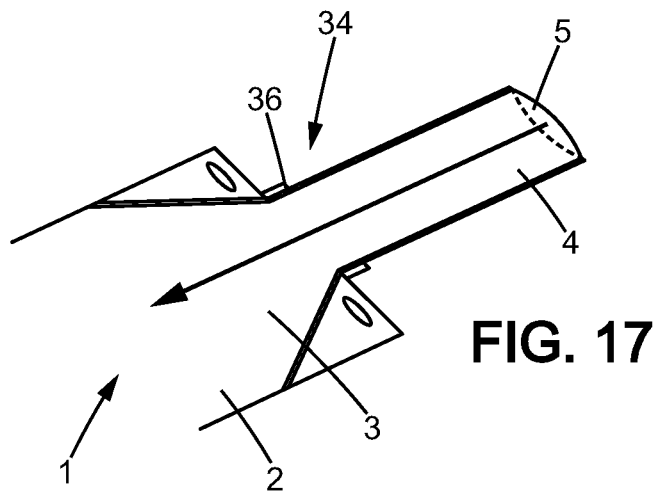
FIG. 17 represents a step of the method for producing a bag example according to the invention, consisting mainly of tucking the neck inside the bag.

FIG. 17 represents a step of the method for producing a bag example according to the invention, mainly consisting of tucking the neck inside the bag.

The arrow indicates that a part of the long neck 4 will be tucked inside the bag 1, indeed even inside the narrowing 3 and the remainder of the bag 2. This long neck 4 will be tucked inside the bag 1 until it reaches the level of the visual mark 34.

Figure 18:
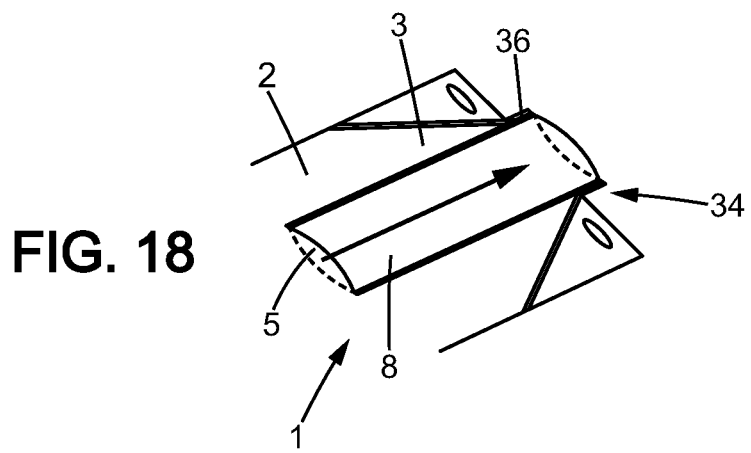
FIG. 18 represents a step of the method for producing a bag example according to the invention, consisting mainly of returning the end of the neck into the tucked part, itself situated in the bag.

FIG. 18 represents a step of the method for producing a bag example according to the invention, mainly consisting of returning the end of the neck into the tucked part, itself situated inside the bag.

The arrow indicates that a part of the long neck 4 tucked inside the bag 1, indeed even inside the narrowing 3 and the remainder of the bag 2, will now be tucked inside this same long neck 4 until it almost comes to the outside of the bag 1, i.e. indeed until it is flush with the visual mark 34.

Figure 19:
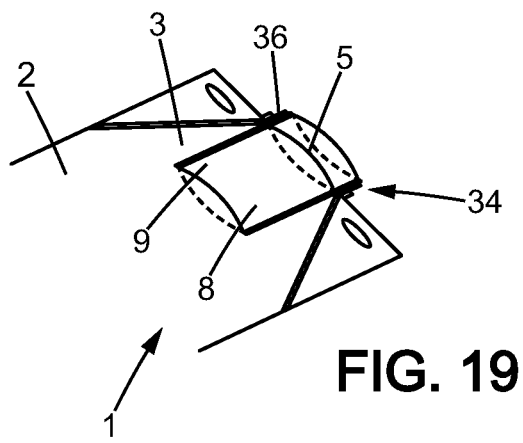
FIG. 19 represents a bag example according to the invention, ready to be secured to a connector.

FIG. 19 represents a bag example according to the invention, ready to be secured to a connector.

The part of the long neck 4 tucked inside itself is flush with the visual mark 34. In particular, the end 9 of the neck 4 is ready to be pulled towards the outside by passing through the connector, once it has been installed, to be unrolled inside the chamber to which the connector has been secured.

Figure 20:
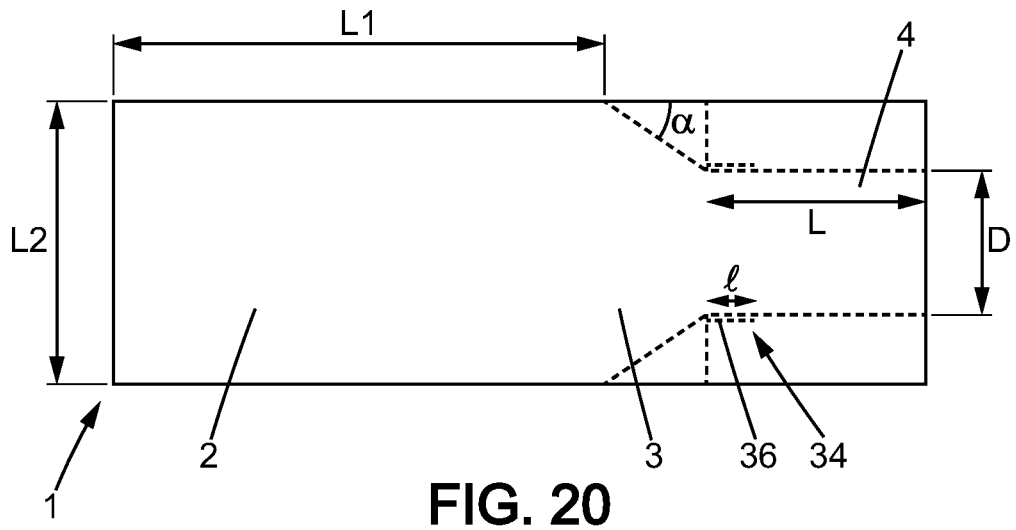
FIG. 20 represents examples of dimensions of a bag according to the invention, corresponding to the first and second examples of type of method for producing the bag.

FIG. 20 represents examples of dimensions of a bag according to the invention, corresponding to the first and second examples of type of method for producing the bag.

The length l of additional weld 36 is between 80 mm and 120 mm, and preferably equals 100 mm. The length L of the neck 4 is between 100 mm and 900 mm, preferably between 300 mm and 900 mm, even more preferably between 600 mm and 900 mm. The diameter D of the neck 4 is between 300 mm and 400 mm, and for example equals 340 mm. The length L1 of the body 2 of the bag 1 is between 900 mm and 1100 mm, and for example equals 1000 mm. The width L2 of the bag 1 at the body 2 thereof is between 300 mm and 600 mm, preferably between 400 mm and 500 mm. The angle α of the narrowing 3 for example equals around 45 degrees.

Figure 21:
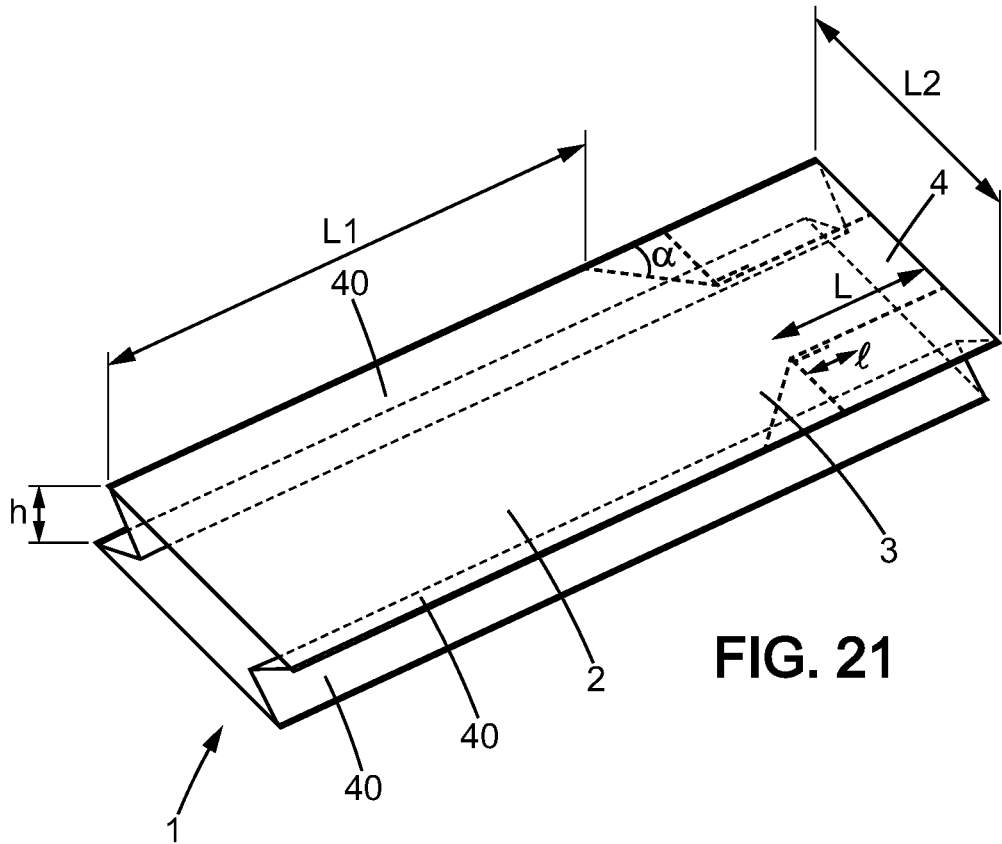
FIG. 21 represents examples of dimensions of a bag according to the invention, corresponding to the third example of type of method for producing the bag.

FIG. 21 represents examples of dimensions of a bag according to the invention, corresponding to the third example of type of method for producing the bag.

Figure 22:
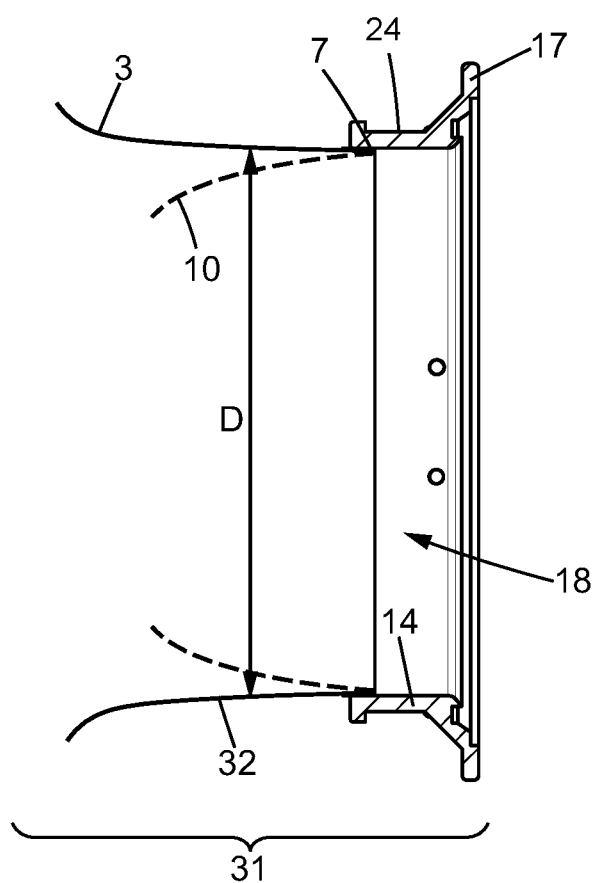
FIG. 22 schematically represents a cross-sectional view of an example of an embodiment of a biopharmaceutical container with part of a bag secured to an inner perimeter of a connector.

FIG. 22 schematically represents a cross-sectional view of an example of an embodiment of the biopharmaceutical container 31 with the part of the bag 1 that is secured to the connector 14 being secured to an inner perimeter of the connector 14.

The dimensions are similar or equal to those of FIG. 20. The height h of the side folds 40 is between 20 mm and 60 mm, and for example equals 40 mm.

Of course, the present invention is not limited to the examples and to the embodiment described and represented, but it is likely for numerous variants accessible to a person skilled in the art.

The invention claimed is:

1. A biopharmaceutical container, comprising:
a connector configured to be secured to a chamber connector,
a bag, serving as a receptacle, comprising a wall with a part of which secured to the connector; and
a flexible sleeve tucked inside the bag and operable to be unrolled out from the bag through the connector, and
wherein:
the sleeve forms part of the bag;
said part of the wall secured to the connector comprises a fold of the wall of the bag;
the wall of the bag forms a body of the bag extending from one side of the fold, and the sleeve extending from the other side of the fold; and
the sleeve comprises a neck portion of reduced size extending from the body of the bag and forms a free end of the bag with an open opening that is in communication with an interior of the bag.

2. The biopharmaceutical container according to claim 1, wherein:
said part of the wall secured to the connector is secured around the connector.

3. The biopharmaceutical container according to claim 1, wherein:
said part of the wall secured to the connector is secured to an inner perimeter of the connector.

4. The biopharmaceutical container according claim 1, wherein:
the fold of the wall of the bag comprises two portions of the wall of the bag folded onto one another, with no free space between them, said two portions being secured together.

5. The biopharmaceutical container according to claim 4, wherein:
an overmolding is arranged between the connector and the fold, and the fold is welded to the overmolding.

6. The biopharmaceutical container according to claim 5, wherein:
the overmolding comprises a cavity of which the inner shape molds the outer shape of a protuberance on an outer wall of the connector.

7. The biopharmaceutical container according to claim 1, wherein:
the inside of the container is sterile.

8. The biopharmaceutical container according to claim 1, wherein:
the bag is made of flexible plastic.

9. The biopharmaceutical container according to claim 1, wherein:
at least the part of the bag secured to the connector has a symmetry of revolution.

10. The biopharmaceutical container according to claim 1, wherein:
the container is filled with biopharmaceutical materials or biopharmaceutical components or biopharmaceutical products, to transfer into a chamber.

11. The biopharmaceutical container according to claim 1, wherein:
the connector has a diameter of between 80 mm and 300 mm.

12. A biopharmaceutical container, comprising:
a connector configured to be secured to a chamber connector;
a bag, serving as a receptacle, comprising a wall that forms a body, one part of the wall being secured to the connector; and
a flexible sleeve tucked inside the bag that is operable to be unrolled out from the bag through the connector,
wherein:
the sleeve forms an end portion of the bag with an open opening that is in communication with an interior of the bag;
the sleeve extends from the body of the bag, and has a greatest dimension that is the same as a dimension of the body portion, the greatest dimension of the sleeve being between 100 mm and 300 mm;
said part of the wall that is secured to the connector is a fold of the wall of the bag; and
the body extends from one side of the fold and the sleeve extends from the other side of the fold.

13. A method for using the biopharmaceutical container according to claim 1, comprising:
securing the container against an opening of a chamber,
unrolling the flexible sleeve from inside the bag to outside of the body of the bag through the connector and through the opening of the chamber, and
transferring contents from within the bag of the container to within the chamber through the unrolled sleeve.

14. The method for using a biopharmaceutical container according to claim 13, comprising:
between the securing and the unrolling, opening the connector to connect the interior of the bag and an interior of the chamber, and
after the transferring step, successively: retracting the flexible sleeve; closing the connector; and, disconnecting the container and the chamber.

15. A biopharmaceutical container bag, comprising:
a bag comprising a body serving as a receptacle; and
a part of the bag configured to be secured to a connector of the container bag,
wherein:
a flexible sleeve, which is tucked inside the body of the bag and operable to be unrolled out from the body of the bag through the part of the bag configured to be secured to the connector of the container, forms a portion of the bag and a neck of reduced size extending the body of the bag;
the sleeve forms a free end of the bag with an open opening that is in communication with an interior of the bag;
the part of the bag configured to be secured to the connector of the container is a fold of a wall of the bag; and
the body of the bag extends from one side of the fold and the sleeve of the bag extends from the other side of the fold.

16. A method for using the biopharmaceutical container bag according to claim 15, comprising:
securing the container against an opening of a chamber,
unrolling the flexible sleeve from inside the bag to outside of the body of the bag through the connector and through the opening of the chamber, and transferring the contents between from the bag of the container and the container through the unrolled sleeve.

17. The biopharmaceutical container bag according to claim 15, wherein:
only a portion of a length of the sleeve is tucked inside the body of the bag.

18. The biopharmaceutical container bag according to claim 15, wherein:
the length of the sleeve is between 100 mm and 900 mm.

19. The biopharmaceutical container bag according to claim 15, wherein:
the neck comprises a visual mark representative of the positional limit of the tucked arrangement of the neck inside the body of the bag.

20. The biopharmaceutical container bag according to claim 19, wherein:
the visual mark is the end of a length of a weld along the bag that extends from an end of the neck.

21. The biopharmaceutical container bag according to claim 15, wherein:
the bag comprises a progressive narrowing shape of the body of the bag as it extends to the sleeve or the neck of the bag.

22. The biopharmaceutical container bag according to claim 15, wherein:
the sleeve has a section at least 4 times smaller than a section of the body of the bag.

23. The biopharmaceutical container bag according to claim 15, wherein:
the sleeve or the neck has a length that is equal to or greater than one tenth of the length of the body of the bag.

24. A method for producing a biopharmaceutical container, comprising:
producing a bag comprising a body extended by a neck of reduced size, the neck having a free end with an opening,
tucking the neck inside the body of the bag, and thereby forming a fold in a wall of the bag between the body of the bag and the neck of the bag wherein the opening at the free end of the neck is in communication with the body of the bag, and
securing the fold to a connector configured to be connected to a chamber.

25. The method for producing a biopharmaceutical container according to claim 24, further comprising:
filling the container with content;
closing the connector by a door so as to seal the container at the connector; and
sterilizing the container filled with the content.

26. The method for producing a biopharmaceutical container according to claim 24, further comprising:
closing the connector by a door so as to seal the container at the connector;
filling the container with content;
closing a bottom of the bag so as to seal the container at the bottom; and
sterilizing the container filled with the content.

27. The method for producing a biopharmaceutical container according to claim 24, wherein:
the producing of the bag comprises extruding or assembling the bag.

28. The biopharmaceutical container according to claim 4, wherein the two portions of the wall of the bag are welded together.

29. The biopharmaceutical container according to claim 8, wherein the bag is made of flexible non-elastic plastic.

30. The biopharmaceutical container according to claim 7, wherein the sterile interior of the container is formed by the interior of the bag and an interior of the connector.

31. The biopharmaceutical container according to claim 1, wherein the sleeve comprises a base portion that extends from the body of the bag, and an end portion that extends from the base portion to the free end, and wherein the sleeve is tucked into the inside of the bag such that the base portion extends in a first direction that extends from the fold towards the inside of the bag, and the free end portion extends in a second direction that opposes the first direction and extends from the inside the bag toward the fold.

32. The biopharmaceutical container according to claim 31, wherein the end portion of the sleeve is positioned within the base portion of the sleeve when the sleeve is tucked into the inside of the bag.

33. The biopharmaceutical container according to claim 31, wherein the sleeve is folded over upon itself between the base portion and the end portion.

* * * * *